United States Patent
Uruga et al.

(10) Patent No.: US 6,416,994 B1
(45) Date of Patent: Jul. 9, 2002

(54) METHANATION ACTIVITY MEASURING INSTRUMENT

(75) Inventors: Akira Uruga; Seiji Imabayashi; Yasushi Kitagawa; Yoshmitsu Harada, all of Tokyo (JP)

(73) Assignee: Asahi Breweries, Ltd., Tokyo (JP)

( * ) Notice: Subject to any disclaimer, the term of this patent is extended or adjusted under 35 U.S.C. 154(b) by 0 days.

(21) Appl. No.: 09/485,953

(22) PCT Filed: Aug. 25, 1998

(86) PCT No.: PCT/JP98/03768

§ 371 (c)(1), (2), (4) Date: Feb. 17, 2000

(87) PCT Pub. No.: WO99/10739

PCT Pub. Date: Mar. 4, 1999

(30) Foreign Application Priority Data

Aug. 27, 1997 (JP) .............................................. 9-231162

(51) Int. Cl.⁷ ........................... C12M 1/34; C12M 1/107
(52) U.S. Cl. ................ 435/287.5; 435/300.1; 435/303.2; 435/303.3; 422/79
(58) Field of Search ........................... 435/287.1, 287.5, 435/287.9, 288.1, 300.1, 302.1, 303.1, 303.2, 303.3, 801, 807; 422/79; 436/62, 63; 73/19.05, 23.2, 31.04; 210/85, 90, 614

(56) References Cited

U.S. PATENT DOCUMENTS

| | | | |
|---|---|---|---|
| 3,348,409 A | * | 10/1967 | Arthur |
| 3,740,320 A | * | 6/1973 | Arthur |
| 3,861,195 A | * | 1/1975 | Vom Hagen |
| 4,314,029 A | * | 2/1982 | Ohtake et al. |
| 4,650,767 A | * | 3/1987 | Arthur |
| 5,674,702 A | * | 10/1997 | Camilli et al. |
| 5,811,255 A | * | 9/1998 | Hunter et al. |

FOREIGN PATENT DOCUMENTS

| | | | |
|---|---|---|---|
| DE | 197 34 154 A1 | * | 2/1999 |
| JP | 1-312999 A | * | 12/1989 |
| JP | 8-242887 A | * | 9/1996 |
| JP | 8-285837 A | * | 11/1996 |

OTHER PUBLICATIONS

Matsunaga et al. Japanese Language Journal Article, vol. 37, No. 7 (1995), pp. 24–29.*

* cited by examiner

Primary Examiner—William H. Beisner
(74) Attorney, Agent, or Firm—Flynn, Thiel, Boutell & Tanis, P.C.

(57) ABSTRACT

The present invention provides a specific methanogenic activity measuring apparatus, in which a carbon dioxide gas absorbing container 6 is removably accommodated in a pressure vessel 4 with a cover 3 removably set thereon, the pressure vessel 4 is removably accommodated in a thermostatic water bath 7 with a pressure transducer 8 based on the pressure-electricity converting system connected to a recorder 5 attached to the cover 3, and further a supporting member for supporting a carbon dioxide gas absorbing container and a generated gas piping 16 are attached to an external bottom surface and an internal bottom surface of the carbon dioxide gas absorbing container 6 respectively, and gas piping 12 with valves for gas phase replacement to the cover 3 of the pressure vessel 4.

8 Claims, 8 Drawing Sheets

(1) ·············· SAMPLING OF SLUDGE
  ↓
(2) ············ CONDITIONING OF A REACTION LIQUID
              (30 MINUTES)
  ↓
(3) ············ SLUDGE IS PUT IN A PRESSURE
              VESSEL TOGETHER WITH A SPECIFIC
              VOLUME OF REACTION MIXTURE (4 MINUTES)
  ↓
(4) ············ A CARBON DIOXIDE GAS ABSORBING
              CONTAINER IS PLACED IN THE PRESSURE
              VESSEL AND A NaOH SOLUTION IS
              FILLED THEREIN (TIME 0)
  ↓
(5) ············ NITROGEN GAS IS FED FROM A GAS
              PIPING INTO THE PRESSURE VESSEL
              (ABOUT 30 SECONDS)
  ↓
(6) ··············· START OF MEASUREMENT
  ↓
(7) ········ DETERMINATION OF SPECIFIC METHANOGENIC
          ACTIVITY (SLOPE) BY A PRESSURE TRANSDUCER
              (FOR INSTANCE, 4 HOURS)
  ↓
(8) ············ MEASUREMENT OF gVSS OF SLUDGE
              (24 HOURS)

TOTAL      28 HOURS AND 34 MINUTES

(1) ·················· SAMPLING OF SLUDGE (2) ············ SLUDGE AND REACTION MIXTURE ARE PUT IN A FLASK AND KEPT OVERNIGHT UNDER 35°C (12 HOURS)

(3) ··················· START OF MEASUREMENT (4) ···················· DETERMINATION ON SLOPE (SPECIFIC METHANOGENIC ACTIVITY) THROUGH MEASUREMENT FOR 68 HOURS (5) ·········· MEASUREMENT OF gVSS OF THE SLUDGE (24 HOURS)

TOTAL                       44 HOURS

METHANATION ACTIVITY MEASURING INSTRUMENT

FIELD OF THE INVENTION

The present invention relates to a measuring apparatus for measuring specific methanogenic activity of granular sludge used in an anaerobic wastewater processing method.

BACKGROUND TECHNOLOGY

Figure 12:
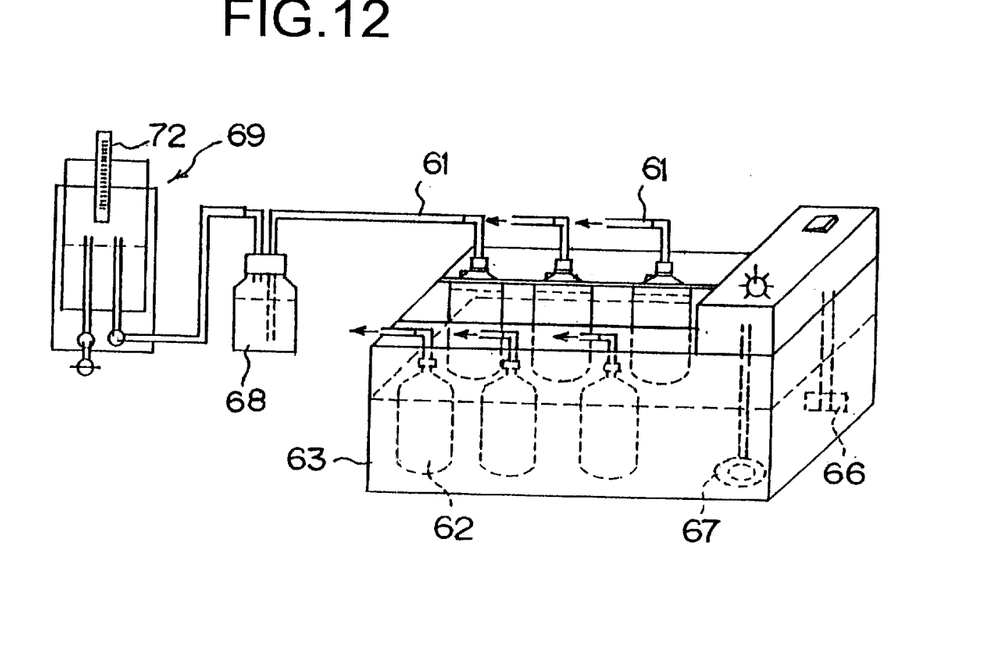
FIG. 12 is a perspective view showing a specific methanogenic activity measuring apparatus based on the conventional technology but similar to that according to the present invention.
Figure 13:
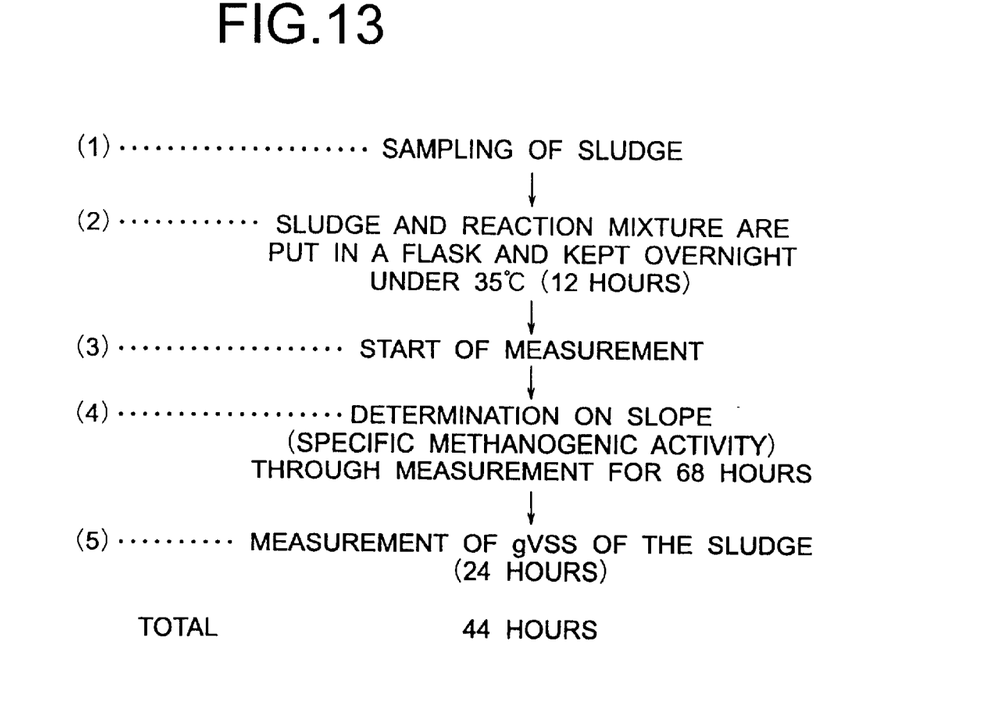
FIG. 13 is a view showing the flow of operations of the apparatus.

As a known measuring apparatus for measuring specific methanogenic activity of sludge, there is that used in a method called as "the vessel method" as disclosed in the publication "Journal of water and Waste (in Japanese) Vol. 37, No. 7 (1995)", which is as shown in FIG. 12 and FIG. 13, and description is made hereinafter for the apparatus. A plurality of narrow-mouthed bottles 62, to each of which a gas conduit piping 61 is disconnectably connected, are placed in water in a thermostatic bath 63 with a stirring member 66 and a heater 67 installed in the thermostatic bath 63, a tip of the gas conduit piping 61 is inserted in a washing gas bottle 68 filled with 1N, NaOH, this washing gas bottle 68 and a gas holder 69 are connected to each other with the gas conduit piping 61, and a scale 72 is attached to the gas holder 69.

An operating sequence when measuring specific methanogenic activity of sludge with the apparatus as described above is shown in an operation flow chart in FIG. 13, and in this flow chart, (1) A first sludge to be measured is sampled, (2) the sampled sludge and a reaction mixture are put in the narrow-mouthed bottle 62 placed in the thermostatic bath 63, and is kept in the state for raising the anaerobic characteristics of the apparatus with the stirring member 66 and heater 67 being operated for 12 hours at 35° C., (3) A gas generated in the narrow-mouthed bottle 62 is guided through the gas conduit piping 61 into the washing gas bottle 68 filled with 1N, NaOH to remove $CO_2$, and then (4) the gas is kept for 6 to 8 hours in the gas holder 69, and during this period up and down movement of the gas holder 69 is visually read with the scale 72 once for every 1 hour to determine specific methanogenic activity (slope) [gCOD], and finally (5) gVSS of the sludge is measured for 24 hours.

Then based on the specific methanogenic activity (slope) and a quantity of sludge [gVSS], a quantity of methane gas formed per day [gCOD/gVSS/d] is computed according to a sequence similar to that according to the present invention as described hereinafter.

PROBLEMS TO BE SOLVED BY THE INVENTION

By the way, with the measuring apparatus as described above, gas phase replacement is not taken into account in the measurement of specific methanogenic activity as described above, and a long period of time is required for raising the anaerobic characteristics of the apparatus. Totally, 44 hours are required for sampling of the sludge, and during this period of time an operator is required to continuously monitor a gauge without leaving the measuring apparatus, which is a heavy work load to the operator. In addition, measurement values are visually read by the operator from the scale, so that the read values may be inaccurate, and further careful operations are required to keep the narrow-mouthed bottle without causing movement thereof. When measuring sludge with a low specific methanogenic activity, sometimes a NaOH aqueous solution may flow in the reverse direction from a gas holder to the narrow-mouthed bottle with the specific methanogenic activity computed manually by the operator, which requires complicated operations and makes it difficult to quickly compute the specific methanogenic activity or to determine whether measured values on the specific methanogenic activity are acceptable or not.

It is an object of the present invention to provide a specific methanogenic activity measuring apparatus, which can solve the problems in the conventional type of specific methanogenic activity measuring apparatus as described above, requires only a short period of time for raising the anaerobic characteristics, finishes all steps from sampling sludge up to measurement, and also which can automatically record a result of measurement without requiring an operator to stay near the measuring apparatus and continuously monitor the gauges, and resultantly, which does not give a large work load to the operator, nor requires the operator to pay minute attentions for statically keeping the reaction vessel, and further, in which the NaOH solution never flows in the reverse direction into the reaction vessel when measuring sludge with low specific methanogenic activity, the operator is not required to manually compute the specific methanogenic activity, the activity can quickly and easily be computed, and further determination can be made as to whether the measured specific methanogenic activity value is acceptable or not.

MEANS FOR SOLVING THE PROBLEMS

To achieve the objectives as described above, the invention provides a specific methanogenic activity measuring apparatus having a measuring means for measuring specific methanogenic activity of sludge in anaerobic wastewater or soil processing and a recording means, and the measuring apparatus has a pressure vessel with a cover removably attached thereto, a carbon dioxide gas absorbing container, and a thermostatic bath with the pressure vessel removable placed therein as the measuring means, in which a pressure transducer based on the pressure-electricity converting system connected to the recorder is attached to the cover, a supporting member for the carbon dioxide gas absorbing container is attached to an external bottom surface of the carbon dioxide gas absorbing container, a gas piping for venturation penetrating an internal surface of the container, and further a gas piping with a valve for gas phase replacement to a cover of the pressure vessel respectively, and in the invention, a magnetic stirrer is attached to the internal bottom surface of the pressure vessel.

The inventions provide the advantages that the time required for raising the anaerobic characteristics of the apparatus is short, all steps from sampling sludge up to final measurement can be finished within a short period of time, also the apparatus itself can automatically record a result of measurement, an operator is not required to stay near the apparatus for continuously monitoring the gauges, thus the work load of the operator is reduced, and further, an accurate result of measurement can be obtained, minute attentions are not required for statically keeping the reaction vessel, and the NaOH solution never flows in the reverse direction into the reaction vessel when measuring sludge with a low specific methanogenic activity.

The invention also provides a screen display unit having a computing section for automatically computing a quantity of methane formed per day [gCOD/gVSS/d] from information on pressure detected by a pressure transducer based on a pressure-electricity converting system in the measuring means as a recording means and a display section for displaying a computed value processed by the computing section; wherein the computing section measures changes in pressure for a specified period of time for determination according to a pressure signal from the pressure transducer in the measuring means, converts the slope of the pressure change to a historical change in a quantity of formed gas and also to a unit [gCOD/h] which can be expressed as a load corresponding to a methane gas forming rate per hour x[ml], computes a methane gas forming rate per day for one unit volume of sludge by dividing the converted methane gas forming rate x[gCOD/h] by a total volume of sludge [gVSS] used for measurement; the computing section has an A/D convertor for converting a pressure signal from the pressure transducer in the measuring means to a digital signal, a determination time counter for manually setting a determination time therein and numerically displaying a determination time, a gVSS counter for manually setting a gVSS of sludge therein and numerically displaying the gVSS of the sludge, and a control section for computing a methane forming rate [gCOD/gVSS/d] per day according to the pressure signal from the A/D converter, a determination time from the determination time counter, and a gVSS of the sludge from the gVSS counter, or has, in place of the determination time counter and gVSS counter, a keyboard for entering a determination time and a gVSS for the sludge, a screen display unit for displaying on the screen the determination time and the gVSS of the sludge entered from the keyboard, a timer for counting a determination time inputted from the keyboard, and a memory for storing therein a determination time and a gVSS and enabling the control section to read and fetch data stored therein; and the display section comprises a plurality of lamps used for comparing a value of a methane forming rate [gCOD/gVSS/d] computed by the computing section to a threshold value and displaying a result of comparison by turning ON or OFF discretely, and further, the display section compares the value of methane forming rate [gCOD/gVSS/d] computed to the computing section to a criteria for determination and displays on the screen whether the result is acceptable or not.

In these inventions, a determining unit in the specific methanogenic activity measuring apparatus automatically computes a methane forming rate per day [gCOD/gVSS/d] from information on pressure detected by a pressure transducer based on the pressure-electricity converting system in the measuring means, and displays the computed value. Namely, pressure change during a specified period of time for determination is measured according to a pressure signal from the pressure transducer, and the slope of the pressure change is converted to a historical change in the gas forming rate. Then the value is converted to a value [gCOD/h] which can be expressed as a load corresponding to a methane gas forming rate per hour x[ml]. This converted methane gas forming rate x[gCOD/h] is divided by a total quantity of sludge [gVSS] used for measurement to obtain a methane gas forming rate per day for one unit quantity of sludge for computing a methane forming rate per day [gCOD/gVSS/d], so that an operation is not required to manually compute a methane forming rate and the rate can quickly and easily be computed, and further whether a measured methane forming rate is accepted or not can be determined.

DETAILED DESCRIPTION OF THE EMBODIMENTS

For better understanding of the present invention, detailed description is made hereinafter for embodiments of the present invention with reference to the attached drawings.

Figure 1:
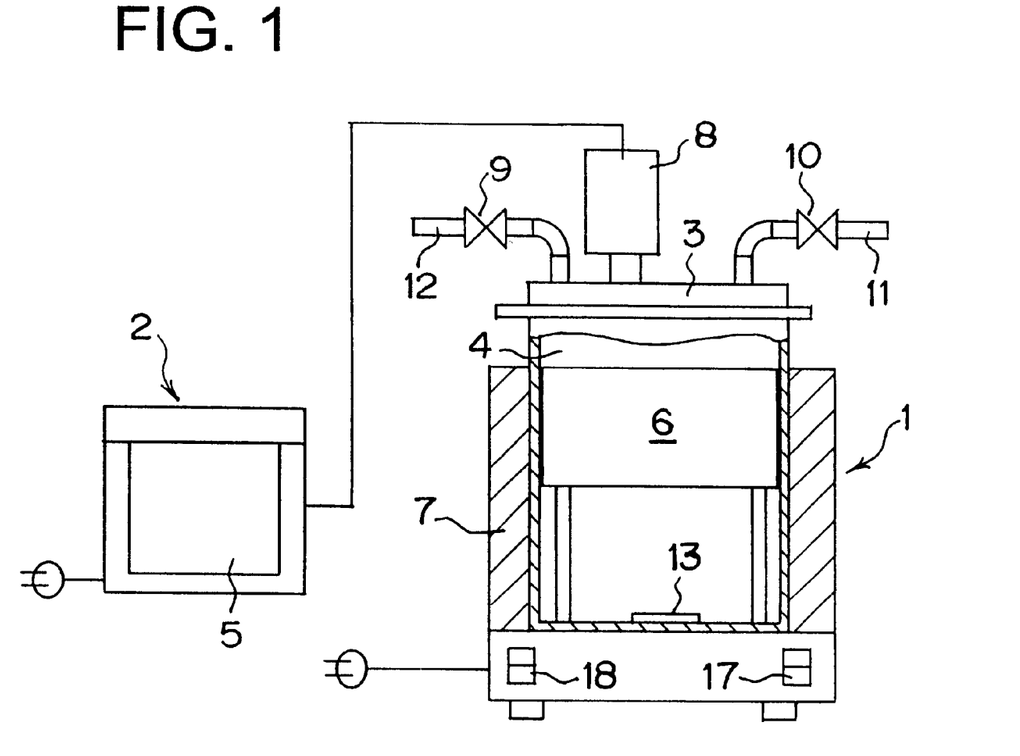
FIG. 1 is a partial sectional front view showing Embodiment 1 of the present invention.
Figure 2:
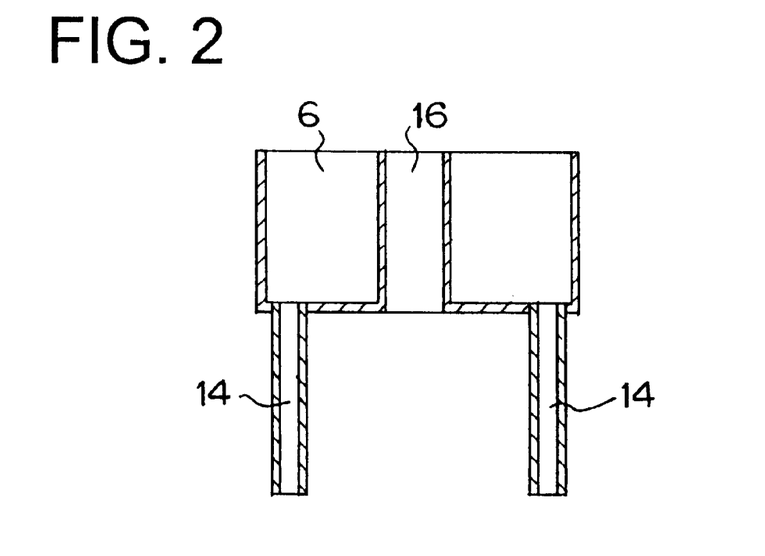
FIG. 2 is a front view showing a longitudinal cross-section of a carbon dioxide absorbing container according to Embodiment 1.

The specific methanogenic activity measuring apparatus according to Embodiment 1 of the present invention shown in FIG. 1 and FIG. 2 comprises a measuring means 1 and a recording means 2, and the measuring means 1 has a pressure vessel 4 with a cover 3 removably attached thereto, a carbon dioxide absorbing container 6 removably accommodated in the pressure vessel 4, and a thermostatic bath 7 with a stirrer removably accommodated in the pressure vessel 4 with a pressure transducer 8 based on the pressure-electricity system connected to the recording means 2 and gas pipings 11, 12 having a pair of valves for gas phase replacement 9, 10 coupled to the cover 3, and a magnetic stirrer 13 is attached to an internal bottom surface of the pressure vessel 4.

A support piping 14 for supporting the carbon dioxide absorbing container 6 is attached to an external bottom surface of the carbon dioxide absorbing container 6, and gas piping 16 for ventilation penetrating through a bottom surface thereof is provided at a central portion of an internal bottom surface of the container. A magnetic stirrer switch 17 for starting a driving unit for running the magnetic stirrer 13 not shown in the figure is provided in the thermostatic water bath 7.

Figure 3:
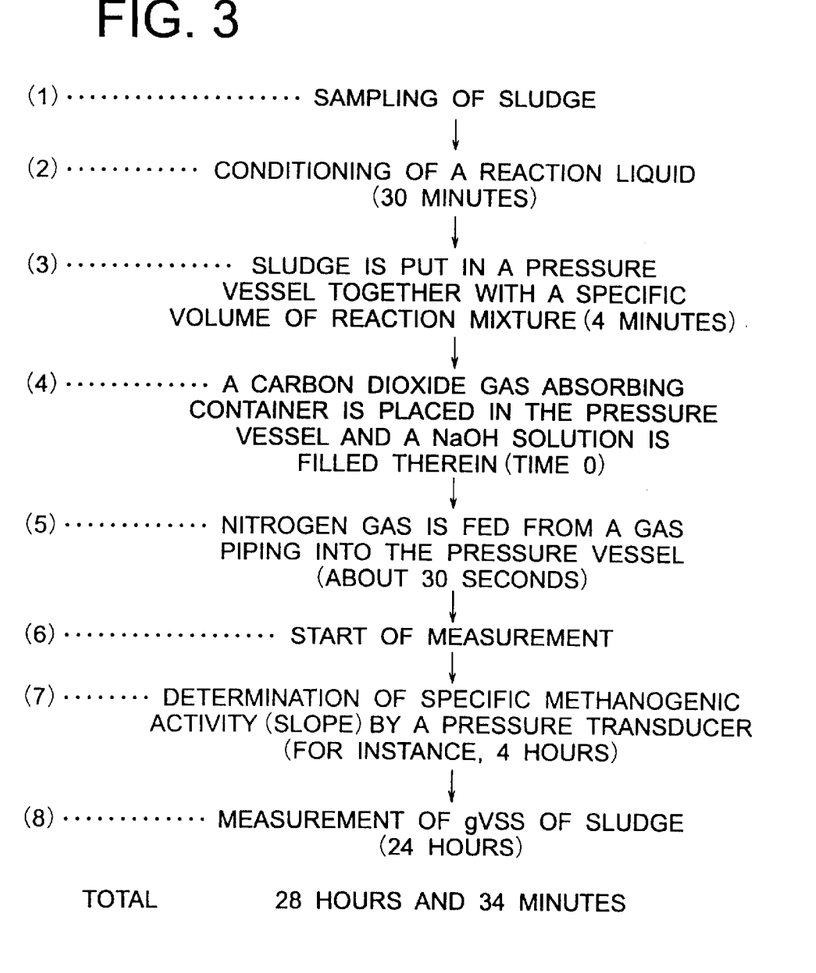
FIG. 3 is a flow chart showing operations of the carbon dioxide absorbing container.

With the measuring apparatus, an operating sequence when measuring specific methanogenic activity of sludge is shown with passage of time in an operation flow chart in FIG. 3, and in this operating sequence, (1) water is poured into the thermostatic water bath 7 of the measuring apparatus 1 by an operator with the temperature of the water in the thermostatic water bath 7 adjusted to 35° C. by turning the heating switch 18 ON;

(2) then the cover 3 for the pressure vessel 4 is removed, and a specified quantity of sludge and a reaction mixture (50 ml of sludge and 450 ml of reaction liquid, totally 500 ml) are poured into the vessel for 1 minute;

(3) then the carbon dioxide absorbing container 6 is placed in the pressure vessel 4 with 20 ml of 20% sodium hydroxide solution filled in the carbon dioxide absorbing container 6 filled in the carbon dioxide gas absorbing container 6 to remove $CO_2$, and then only methane gas is an object for measurement (time 0);

(4) the cover 3 is set on the pressure vessel 4, the valves 9, 10 for gas phase replacement are opened to feed nitrogen gas from one of the gas piping 11 into the pressure vessel 4 to raise the anaerobic characteristics of the apparatus, and air is exhausted from the other ventilation piping 12 to replace the air in a hollow section of the pressure vessel 4 with nitrogen gas for around 0.5 minutes;

(5) then the two valves 9, 10 for gas phase replacement are closed, the pressure vessel is inserted into the water thermostatic water bath 7 at he temperature of 35° C. with the stirrer switch 17 turned ON to start operation of the magnetic stirrer 13 and mix the sludge and reaction mixture within the pressure vessel 4, and the temperature within the pressure vessel 4 is stabilized within around 3 minutes;

(6) then the operator turns ON a switch of the recording means 2, inputs pressure values detected during, for instance, 4 hours with the pressure transducer 8 based on the pressure-electricity converting system into the recorder 6, and terminates measurement, and (7) thus specific methanogenic activity [gCOD/gVSS/d] is measured and computed by spending 24 hours as described in the example described below to finish the entire operating sequence measurement, and in this case a time required for the entire sequence for measurement is around 28 hours and 34 minutes As described above, when measuring the specific methanogenic activity, information on the pressure detected by the pressure transducer 8, based on the pressure electricity converting system provided between the pressure vessel 4 and recording unit 2, is inputted into the recording means 2 for measurement, so that no work load is required for the operator, and an excellent result of measurement can be obtained with a work load for an operator substantially reduced, and in addition, accurate information on measurement can be obtained.

EXAMPLE 1

Specific operating sequences in the "method of measuring a volume of sludge" and "method of adjusting a reaction mixture" in step (2) above in measurement of specific methanogenic activity of granular sludge as described above is as follows.

Method of Measuring a Volume of Sludge

Figure 4:
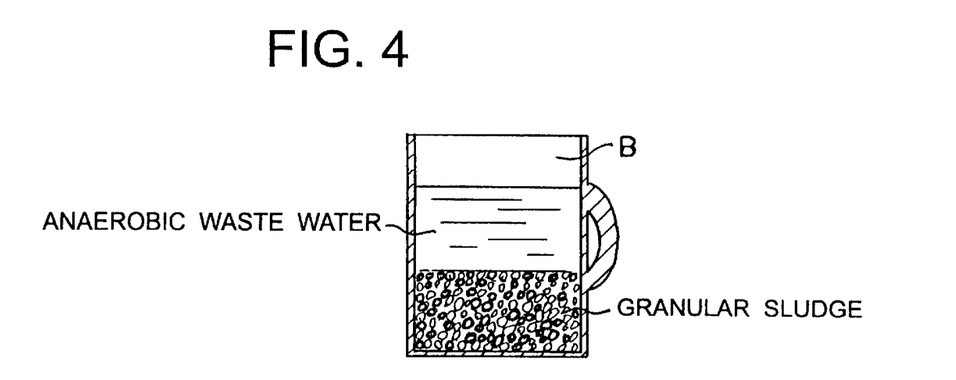
FIG. 4 is an explanatory view showing an initial state in an example of a method of weighing sludge in Embodiment 1.

1) Anaerobic wastewater containing granular sludge is sampled from an upflow anaerobic sludge blanket tank (UASB tank), and is put in a wide-mouthed beaker B with a capacity of 2L as shown in FIG. 4.

Figure 5:
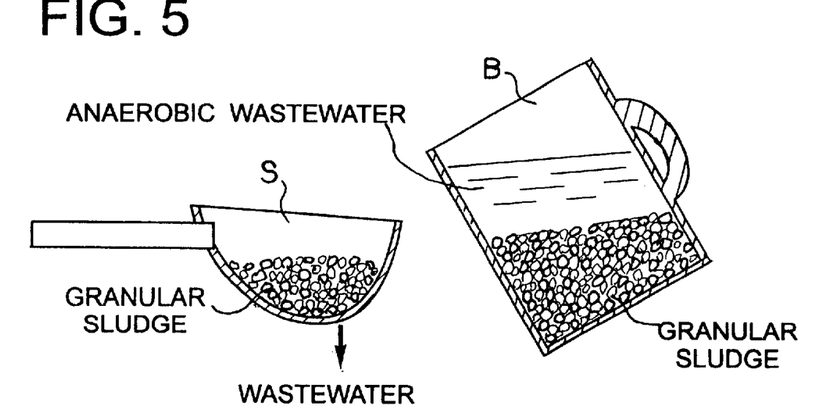
FIG. 5 is an explanatory view showing an intermediate state in the example of weighing sludge.

2) The anaerobic wastewater is poured into a filtering vessel S as shown in FIG. 5 to remove the wastewater and minute suspended materials to some degree.

Figure 6:
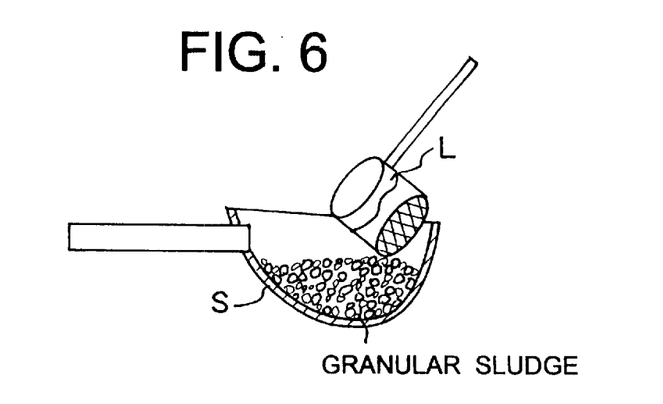
FIG. 6 is an explanatory view showing a final state in the example of weighing sludge.

3) The granular sludge obtained through the sequence as described above is scooped with a dipper having a capacity of 50 ml to accurately obtain an dipper-full of sludge.

4) The granular sludge measured and obtained as described above is put in the pressure vessel 4 together with 450 ml of reaction mixture adjusted as described below.

Method of Adjusting a Reaction Mixture

① Constituent Solution of the Reaction Mixture

Solution A (buffer): A solution containing a buffer agent condensed to a 100 times higher density as compared to that in ordinary use (pH=7.0), an indicator, vitamins, and rare metals.

Solution B (reductant): 2.5% sodium sulphate aqueous solution, which is used to adjust a reaction liquid into an anaerobic state.

Solution C (reductant): 2.5% stain chloric salt aqueous solution, which is used to guide a reaction liquid into an aerobic state.

Solution D (reductant): 128/L sodium acetate aqueous solution (pH=7.0), 10 ml of which is equivalent to 1 gCOD.

The reaction mixture is diluted and mixed with distilled water according to the following procedure for adjustment.

② Adjustment Procedure 1) 5 ml of solution A is put with a pipet into an empty screw-mouthed bottle.

2) Accurately, 425 ml of service water is sampled with a 500 ml messcylinder, and poured into t he screw-mouthed bottle.

3) Then, totally, 10 ml of solution D (by 5 ml twice) is poured into the threaded-mouth bottle.

4) 5 ml of solution B is quickly poured with a pipet into the threaded-mouth bottle.

5) Then 5 ml of solution C is quickly poured with a pipet into the bottle.

6) After the steps 4) and 5) above are finished, a cap for the threaded-mouth bottle is tightly closed.

(Note 1): After the step 6, the color of the solution changes from blue to pink and then to transparent in association with reduction of dissolved oxygen in the mixture.

(Note 2): A total time required for conditioning is in a range from around 15 to 30 minutes.

(Note 3): A total quantity of reaction mixture is 450 ml.

EXAMPLE 2

Computing Sequence

A sequence of computing specific methanogenic activity [gCOD/gVSS/d] in the example above is as described below.

1) Pressure change for 4 hours from the start of measurement is monitored.

2) Slope of the pressure change obtained as described above is computed to hourly change in a volume of formed methane gas:

$$x = \text{Dimensions of a capacity of the pressure vessel} \times y \quad (1)$$

wherein x[ml/h]: Methane gas forming velocity, and y[kgf/cm$^2$/h]: Slope of pressure change 3) A volume x[ml] of methane formed per hour obtained as described above is converted to a unit [gCOD/h] which can be expressed as a corresponding load. In a case of methane, 1 [gCOD] corresponds to 350 [ml].

4) A volume of methane formed per day for one unit volume of sludge is computed by dividing the volume of methane x[gCOD/h] described above by the total volume of sludge [gVSS] used in the measurement.

5) Finally, a volume of methane formed per day [gCOD/gVSS/d] is computed.

Example of Computing

A practical case of computing a volume of formed methane according to the above-described sequence is described below.

a) From the above-described computing sequence, it is understood that specific methanogenic activity (slope) when the measured pressure change for 4 hours with the recording means 2 from start of measurement is 0.3 [kgf/cm$^2$], the specific methanogenic activity (slope) is computed as follows:

$$0.3 \div 4 = 0.075 [\text{kgf/cm}^2/\text{h}]$$

b) Then, assuming that a capacity of the pressure vessel is 341 [cm$^3$], a volume of formed gas is computed by converting the slope of pressure change to hourly change in a volume of formed gas according to the equation (1) in the computing step 2) as follows:

$$\text{Volume of formed gas } x = 341 \times 0.0756, \text{ namely } x = 25.58 [\text{ml/h}]$$

c) Herein, by converting the volume x[ml] for methane gas formed per hour to the unit [gCOD/h] expressing a corresponding load according to the step 3) above, the specific methanogenic activity (slope) is computed as follows:

$$25.28 \div 350 = 0.073 [\text{gCOD/h}]$$

d) Then, assuming that the total volume of sludge used in measurement is 4.22 [gVSS], a volume of methane formed per day for one unit volume of sludge is computed according to the step 4) above as follows:

$$0.073 \div 4.22 = 0.0173 [\text{gCOD/gVSS/h}]$$

e) Then, a volume of methane formed per day [gCOD/gVSS/d] is computed according to the step 4) above as follows:

$$0.0173 \times 24 = 0.415 [\text{gCOD/gVSS/d}]$$

This is a value indicating the specific methanogenic activity to be obtained.

Figure 7:
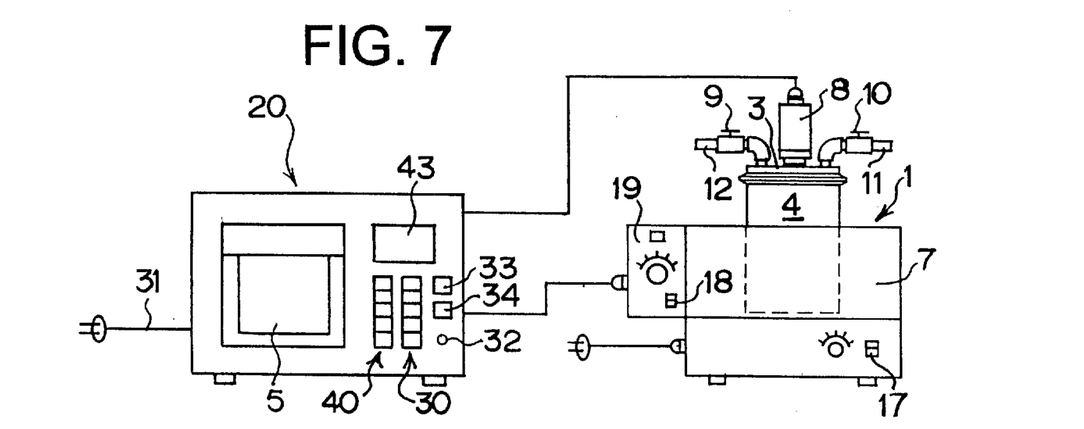
FIG. 7 is a front view showing Embodiment 2 of the present invention.
Figure 8:
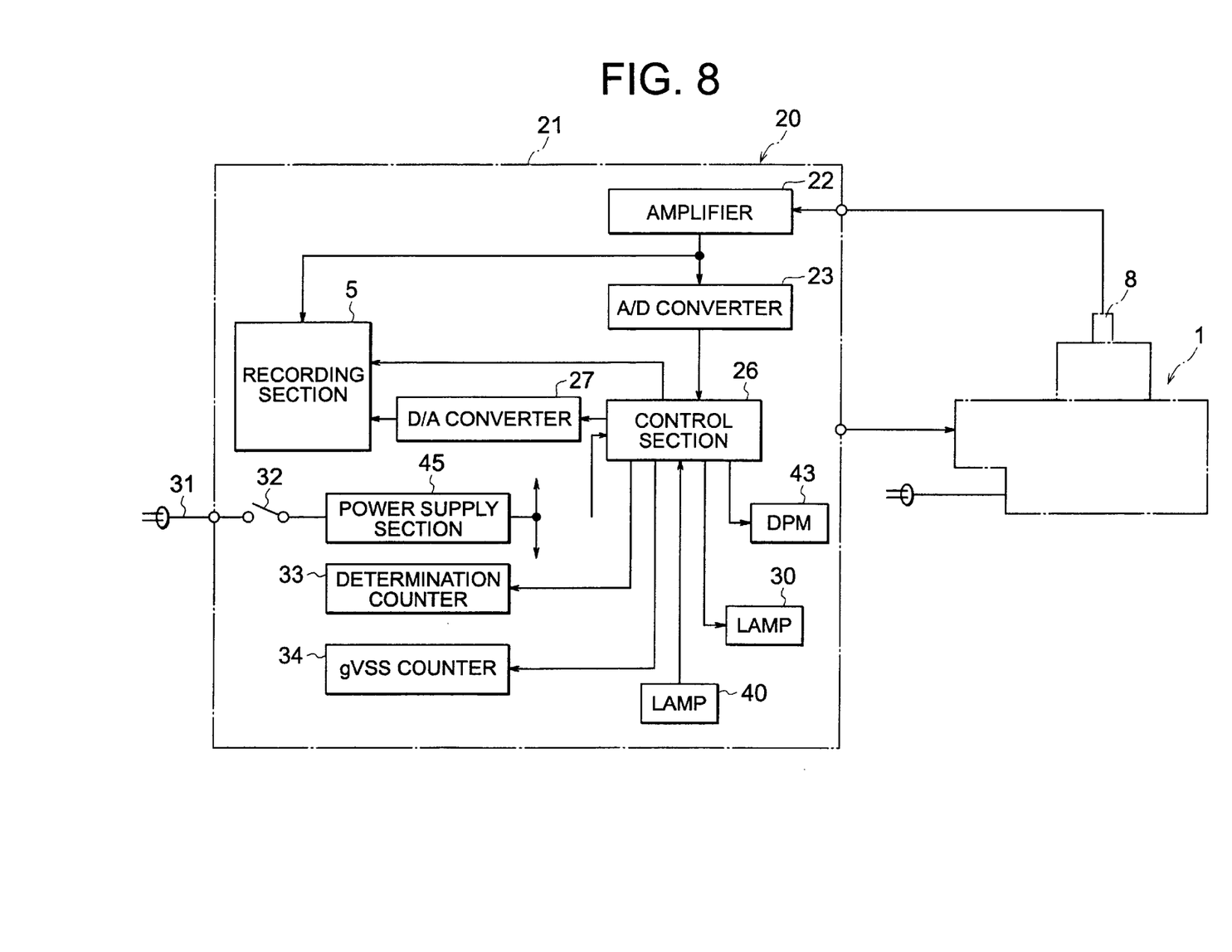
FIG. 8 is a block diagram showing the configuration of an automatic determining means in Embodiment 2.
Figure 9:
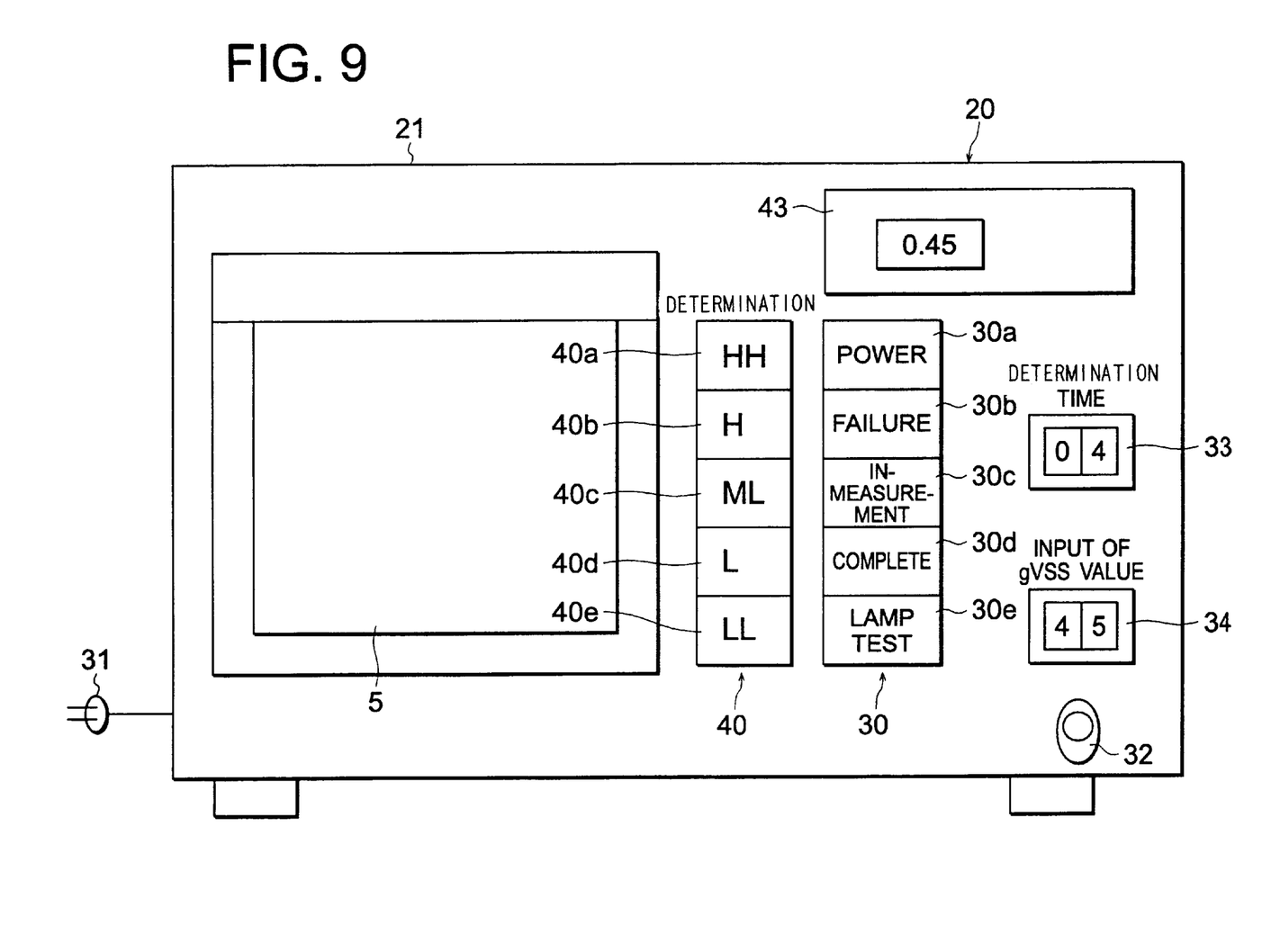
FIG. 9 is a view showing the appearance of the automatic determining means.

Embodiment 2 of the present invention showing in FIG. 7 to FIG. 9 is different from Embodiment 1 in that an automatic determining unit 20 is provided in place of the recording means in Embodiment 1, and a heating switch 18 is provided in the measuring means 1. This automatic determining means 20 has a basic body 12 of the determining unit, and this basic body 21 comprises an amplifier 22 for amplifying a pressure signal outputted from the pressure transducer 8 as shown in FIG. 8, an A/D converter 23 for converting the amplified pressure signal from this amplifier 22 to a digital signal, and a control section 26 for controlling each component and especially providing controls for automatic measurement of specific methanogenic activity. The control section 26 provides controls for computing a volume of methane formed per day [gCOD/gVSS/d] according to data on determination time and a gVSS of sludge provided from the gVSS counter.

Further, the basic body 21 of the measuring means comprises a D/A converter 27 for converting data from the control section 26 to an analog signal and sending the analog signal to the recorder 5, a determination time counter 33 for manually setting determination time in the control section 26, counting the determination time and numerically displaying the determination time, and a gVSS counter 34 for manually setting a gVSS volume of sludge in the control section 26 and numerically displaying the gVSS volume of sludge.

Further, the main body 21 of the measuring means comprises a DPM 43 for displaying such data as specific methanogenic activity obtained as described above (corresponding to a digital panel meter, a digital display unit, or a screen display unit as claimed herein), five pieces of lamps 30a to 30e each lighting up for indicating contents of determination for specific methanogenic activity value, five pieces of limps 40a to 40e lighting up for indicating contents of determination on a specific methanogenic activity value step by step, a power switch 32 for turning ON/OFF the power 31, and a power supply section 45 for supplying a DC current to each section of the basic body 21 of the determining means. It should be noted that other various types of instruction switch are provided but are not shown herein. The instruction switches include a switch for instructing a lamp test or a reset switch for instructing completion of measurement and start of the test measurement.

The lamps 30a to 30e indicate operational states as shown in FIG. 9, and comprise the power lamp 30a lighting up when power is turned ON, a failure indicating lamp 30b lighting up for indicating a failure, an in-measurement indicating lamp 30 lighting up for indicating that measurement is being executed (the basic body 21 of the determining means is operating), a measurement completion indicating lamp 30d lighting up for indicating that measurement has been finished, and a lamp test indicating lamp 30e lighting up for indicating whether each lamp is working normally or not.

The lamps 40a to 40e indicate a result of comparison of a measured specific methanogenic activity value to a criteria for determination previously set in the control section 26 in five stages. The 5-stage indicator lamps consist of the HH-display lamp 40a lighting up and displaying "HH: Quite excellent", MH-display lamp 40b lighting up and displaying "MH: Relatively better" ML-display lamp 40c lighting up and displaying "ML: Relatively worse", L-display lamp 40d lighting and displaying "L: Not good", and LL-display lamp 40e lighting up and indicating "LL: Extremely bad".

In the figure, the determination time counter 33 and gVSS counter 34 are those turned for setting on the panel, but other configuration is allowable. For instance, the configuration is allowable in which there are provided a keyboard for entering determination time and a gVSS rate of sludge, a screen display unit for displaying the determination time and gVSS rate of sludge entered from the keyboard on the screen, a timer for counting the determination time entered from the keyboard, and a memory for storing therein the determination time and gVSS of sludge from which the control section reads out and fetches the stored data.

Next description is made at first for general operations of the basic body 21 of the determining means having the configuration as described above, and then for a sequence of operations for measuring specific methanogenic activity of granular sludge.

When the power switch 32 is turned ON, power is supplied from the power supply section 45 to the basic body 21 of the determining means, and automatic measurement of specific methanogenic activity of the granular sludge is started. A pressure signal from the pressure transducer 8 is amplified by the amplifier 22, and this amplified pressure signal is converted to a digital signal by the A/D converter 23 and the digital signal is sent to the control section 26. Determination time is set in the control section 26 by manually operating the determination counter 33 for counting the determination time and also numerically displaying the determination time. Also a specified gVSS of sludge is set in the control section 26 by manually operating the gVSS counter 34, and the gVSS of sludge is numerically displayed. According to the determination time and gVSS of sludge set by manually operating the determination time counter 33 and gVSS counter 34 as described above, the control section 26 provides controls for computing the specific methanogenic activity [gVOD/gVSS/d] according to a flow and timing of operations as shown in FIG. 6 and FIG. 7.

The specific methanogenic activity value [gCOD/gVSS/d] computed as described above is converted by the D/A converter 27 to an analog signal and the analog signal is sent to the recorder 5, where the measured value is recorded with such a tool as a pen on recording paper. Also the control section 26 provides controls for discretely lighting up each of the lamps 30 (power lamp 30a, failure displaying lamp 30b, in-measurement display lamp 30c, measurement-completion indicator lamp 30d, and lamp test indicator lamp 30e) in response to an operating state as described detailedly in relation to a sequence of operations for measuring specific methanogenic activity of sludge as described hereinafter. Further, the control section 26 provides controls for displaying a measured specific methanogenic activity value with the DPM 43 as well as for lighting up the lamps 40 (HH-display lamp 40a, MH-display lamp 40b, ML-display lamp 40c, L-display lamp 40d, and LL-display lamp 40e) for displaying contents of the measurement in five stages as detailedly described in the sequence of operations for measuring specific methanogenic activity of sludge hereinafter.

Figure 10:
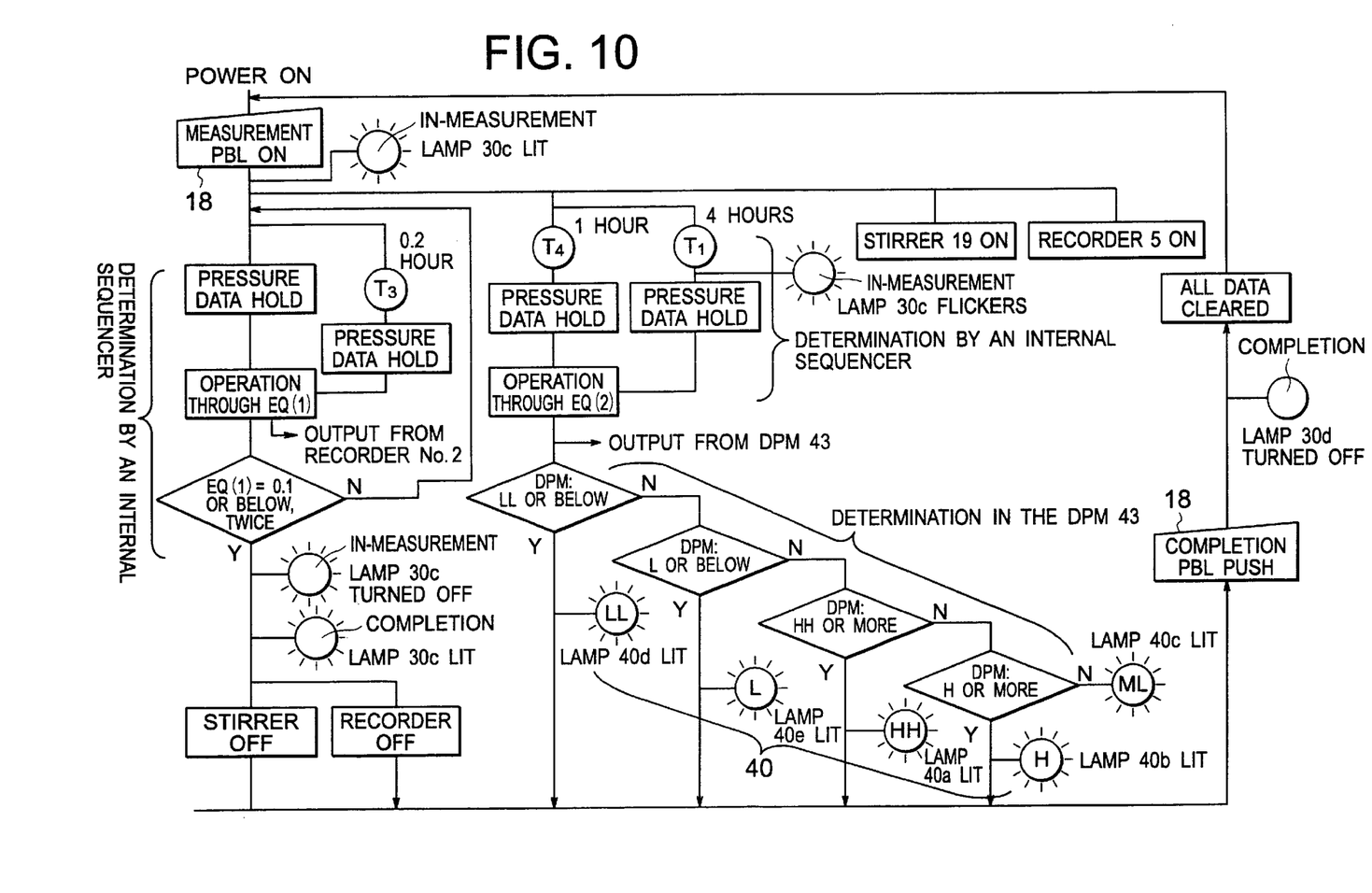
FIG. 10 is a view showing a flow of operations of the automatic determining means.

Description is made hereinafter for a sequence of operations for measuring specific methanogenic activity of sludge with the measuring device as described above with reference to an operation flow chart in FIG. 10.

(A) An operator pours water into the thermostatic water bath 7 of the measuring means 1, and turns ON the heating switch 18 to set the temperature of the water in the thermostatic water bath 7 to 35° C.;

(B) then the operator removes the cover 3 for the pressure vessel 4 and pours a specified volume of sludge and a specified quantity of reaction mixture (50 ml of sludge and 450 ml of reaction mixture, totally 500 ml) in the pressure vessel 4 spending 1 hour;

(C) then the operator places the carbon dioxide absorbing vessel 6 in the pressure vessel 4 and fills 200 ml of 20% sodium hydroxide aqueous solution in the carbon dioxide absorbing vessel 6 to remove $CO_2$ so that only methane gas is measured (time 0), (D) then the operator sets the cover 3 on the pressure vessel 4, opens the valves 9, 10 for gas phase replacement to raise the anaerobic characteristics of the apparatus, and further feeds nitrogen gas from one of the aeration pipes 11 into the pressure vessel 4 and at the same time exhausts the gas from the other gas pipe 12 to replace air within an internal capacity of the pressure vessel 4 with the nitrogen gas by spending around 10 minutes; and (E) Then the operator closes the valves 9, 10 for gas phase replacement, immerses the pressure vessel 4 into the thermostatic water bath 7 having the temperature of 35° C., turns ON the stirrer switch 17 to start the magnetic stirrer 13 and mix sludge and reaction mixture within the pressure vessel, and with the operations described above, in around 10 minutes, inside of the pressure vessel 4 is thermally stabilized, and press-in information (0 to 5 kgf/cm$^2$) is outputted from the pressure transducer 8 as shown in FIG. 8(a).

(F) In this step, the operator turns ON the power switch 32 with the power lamp 30a lit up.

Figure 11:
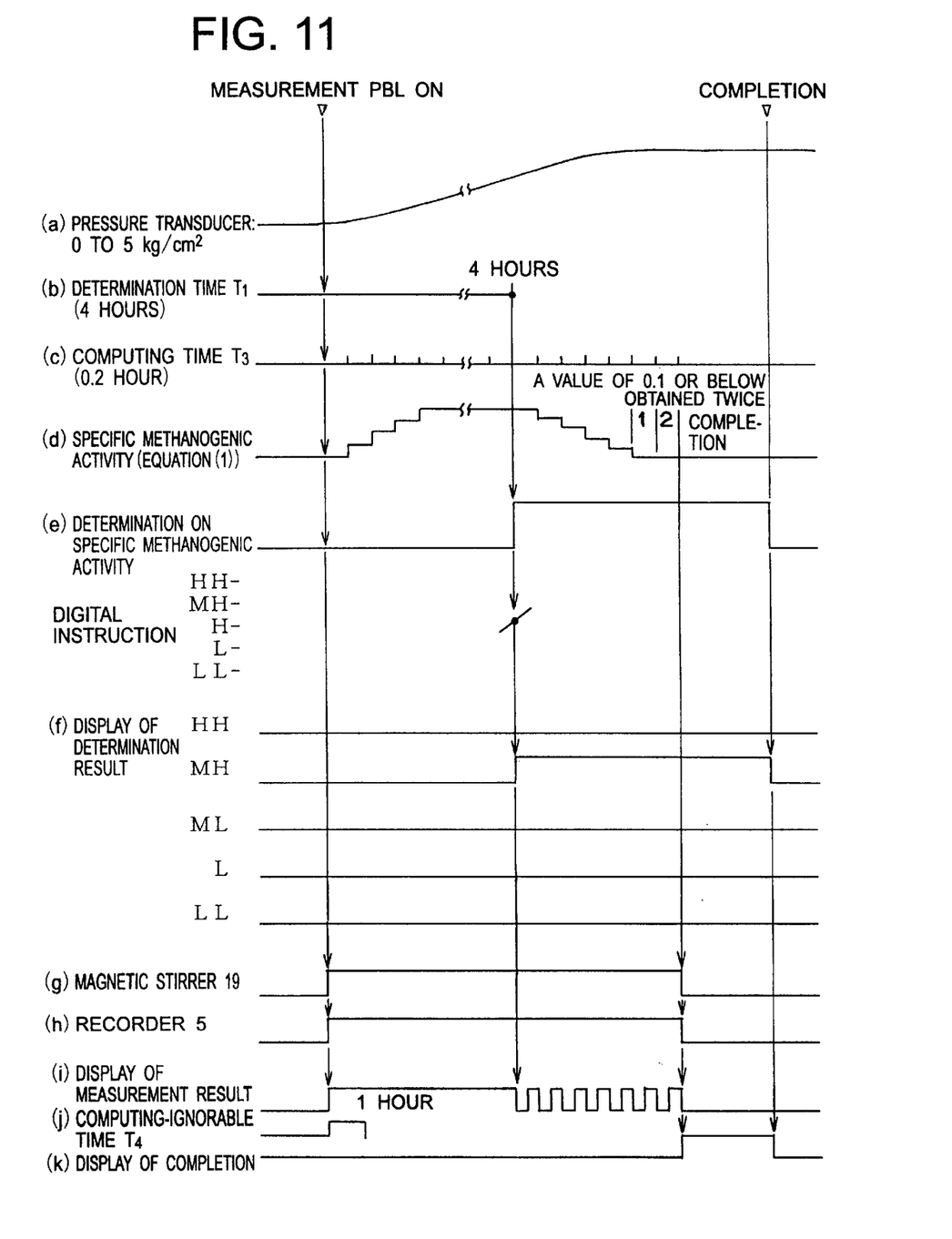
FIG. 11 is a view showing the timing of operations of the automatic determining means.

(G) Then the operator operates the determination time counter 33 to set determination time (4 hours) in the control section 26 as shown in FIG. 11(b) and the time is displayed on the determination time counter 33.

(H) Then the operator operates the gVSS counter 34 to input a gVSS of sludge, and the rate is displayed on the gVSS counter 34.

(J) When the operator lights up on the in-measurement lamp 30c, the stirrer switch 17 is turned ON with a mixing operation of the magnetic stirrer 13 started, and an operation of the recorder 5 for recording is started as shown in FIG. 11(h) under controls by the control section 26.

(K) When there comes the determination time, operations of the determination time counter are finished, and the specific methanogenic activity value $X_1$ computed through the equation (1) under control by the control section 26 as shown in FIG. 11(d) is displayed on the DPM 43.

$$X_1 = \frac{\Delta P_2 \times V \times T_2}{(T_1 - T_4) \times gCOD \times gVSS} \tag{1}$$

In this equation (1), $\Delta P_2$ indicates a pre sure changed from a point of time when the computing-ignorable time has passed until the determination time, V indicates an internal capacity of the pressure vessel, $T_2$ indicates a determination time per day (24 hours), $T_1$ indicates actual determination time (4 hours), $T_4$ indicates a computing-ignorable time (1 hour), gCOD indicates specific methanogenic activity (slope), and gVSS indicates a volume of sludge.

(L) As shown in FIG. 11(i), determination is made as to whether the measured specific methanogenic activity value is acceptable or not according to the specific methanogenic activity value $X_1$ displayed on the DPM 43 as well as to a criteria for determination previously set in the control section 26, and then any of display values HH (High High, Quite excellent), MH (Middle High: Relatively better), ML (Middle Low: Relatively worse, L (Low: Not good), and LL (Low Low: Extremely bad) is displayed on a corresponding one of the determination lamps 40 (40a, 40b, 40c, and 40d).

(M) Then as described above, the specific methanogenic activity value $X_1$ computed through the equation (1) is recorded once for every 12 minutes in the recorder 5 under controls by the control section 26 with the magnetic stirrer 19 started, and when the specific methanogenic activity value $X_1$ of 01 or below are recorded two times successively, the in-measurement lamp 30c is turned out with the completion lamp 30d lit up as shown in FIG. 11(k), and also the stirrer switch 17 is turned OFF with mixing operations of the magnetic stirrer 13 stopped.

(N) When the operator turns OFF the power switch 32, the completion lamp 30d turns out with a displayed value on the DPM 43 cleared, and then the initial state is restored with measurement terminated.

(O) In this measurement, for instance one hour is set as a computing-ignorable time ($T_4$) as shown in FIG. 11(j). Also it is assumed herein that, as shown in FIG. 11(c), computing time ($T_3$) by the control section 26 is executed at a time interval of 0.2 hour (12 minutes).

What is claimed is:

1. A specific methanogenic activity measuring apparatus comprising a measuring means for measuring specific methanogenic activity of sludge or soil during aerobic wastewater treatment and a recording means, the measuring means comprising a thermostatic water bath, a pressure vessel removably accommodated in the water bath, a cover removably placed on the pressure vessel for sealing an open compartment formed therein, a carbon dioxide absorbing container removably disposed in the open compartment, a supporting member attached to the carbon dioxide absorbing container and extending to a bottom wall of the open compartment for supporting said carbon dioxide absorbing container in the open compartment, a pressure transducer attached to the cover for converting a detected pressure into an electrical signal and transmitting the electrical signal to the recording means, ventilation means comprising piping extending through a central portion of the carbon dioxide absorbing container, and gas replacement means attached to the cover and comprising an inlet line having a valve disposed therein for introducing a purge gas into the pressure vessel and an outlet line having a valve disposed therein for exhausting air from the pressure vessel.

2. The specific methanogenic activity measuring apparatus according to claim 1, wherein a magnetic stirrer is attached to an internal bottom surface of the pressure vessel.

3. The specific methanogenic activity measuring apparatus according to claim 1, wherein the recording means comprises a computing section for automatically computing a specific methanogenic activity, gCOD/gVSS/d, from information on the pressure detected by the pressure transducer and a display section for displaying a value computed in the computing section.

4. The specific methanogenic activity measuring apparatus according to claim 3, wherein the computing section measures a change of pressure at a specified determination time according to a pressure signal from the pressure transducer in the measuring means and converts slope in pressure change to hourly change of gas forming rate and also to a unit, gCOD/h, which can be expressed as a load corresponding to the hourly methane gas forming rate xml, and further divides the computed methane gas forming rate xgCOD/h by a total volume of sludge used for the measurement to obtain a methane gas volume per day for one unit of sludge to obtain a volume of methane gas formed per day, gCOD/gVSS/d.

5. A specific methanogenic activity measuring apparatus according to claim 3, wherein the computing section comprises an A/D converter for converting a pressure signal from the pressure transducer in the measuring means to a digital signal, a determination time counter for manually setting a determination time, counting the determination time and numerically displaying the determination time, a gVSS counter for manually setting a gVSS of sludge and numerically displaying the gVSS of sludge thereon, and a control section for providing controls for computing a specific methanogenic activity, gCOD/gVSS/d, to a pressure signal from the A/D converter as well as to the determination time from the determination counter and the gVSS of sludge from the gVSS counter.

6. The specific methanogenic activity measuring apparatus according to claim 5, wherein the functions of the determination time counter and gVSS counter are provided by, a keyboard for entering a determination time and a gVSS of sludge, a screen display unit for displaying the determination time and gVSS of sludge entered from the keyboard on the screen thereof, a timer for counting the determination-time entered from the keyboard, and a memory for storing therein the determination time and gVSS of sludge and enabling the control section to read and fetch the stored data therefrom.

7. The specific methanogenic activity measuring apparatus according to claim 3, wherein the display section comprises a plurality of lamps which light up for indicating a result of a comparison of a value for specific methanogenic activity, gCOD/gVSS/d, computed by the computing section to a criteria for determination in stages.

8. The specific methanogenic activity measuring apparatus according to claim 3, wherein the display section is a screen display unit for displaying a result of a comparison of a value for the specific methanogenic activity, gCOD/gVSS/d, computed by the outputting section to a criteria for determination on a screen thereof.

* * * * *